(12) United States Patent
Kleyman et al.

(10) Patent No.: US 8,521,302 B2
(45) Date of Patent: Aug. 27, 2013

(54) THERMAL TREATMENT APPARATUS

(75) Inventors: Gennady Kleyman, Brooklyn, NY (US); Annaniy Berenshteyn, Ocean, NJ (US); Stuart Trembly, Hanover, NH (US)

(73) Assignee: Expanedoheat, L.L.C., Atlantic Highlands, NJ (US)

( * ) Notice: Subject to any disclaimer, the term of this patent is extended or adjusted under 35 U.S.C. 154(b) by 786 days.

(21) Appl. No.: 12/352,168

(22) Filed: Jan. 12, 2009

(65) Prior Publication Data

US 2009/0182398 A1 Jul. 16, 2009

Related U.S. Application Data

(60) Provisional application No. 61/020,194, filed on Jan. 10, 2008, provisional application No. 61/143,623, filed on Jan. 9, 2009.

(51) Int. Cl.
*A61F 7/00* (2006.01)
*A61F 7/12* (2006.01)
*A61F 2/00* (2006.01)

(52) U.S. Cl.
USPC ............................................ 607/101; 607/96

(58) Field of Classification Search
USPC .......................................... 607/96, 100–102
See application file for complete search history.

(56) References Cited

U.S. PATENT DOCUMENTS

| 4,869,248 | A | | 9/1989 | Narula |
| 5,474,530 | A | | 12/1995 | Passafaro et al. |
| 5,571,088 | A | | 11/1996 | Lennox et al. |
| 5,575,772 | A | | 11/1996 | Lennox |
| 5,653,692 | A | | 8/1997 | Masterson |
| 5,697,925 | A | | 12/1997 | Taylor |
| 5,707,369 | A | * | 1/1998 | Vaitekunas et al. ............. 606/31 |
| 5,800,493 | A | | 9/1998 | Stevens |
| 5,843,144 | A | | 12/1998 | Rudie et al. |
| 5,902,251 | A | | 5/1999 | van Hooydonk |
| 6,041,260 | A | | 3/2000 | Stern et al. |
| 6,159,207 | A | * | 12/2000 | Yoon ............................... 606/41 |
| 6,366,818 | B1 | | 4/2002 | Bolmsjo |
| 6,443,947 | B1 | | 9/2002 | Marko |
| 6,447,505 | B2 | | 9/2002 | McGovern et al. |
| 7,033,352 | B1 | * | 4/2006 | Gauthier et al. ................. 606/33 |
| 2007/0250051 | A1 | * | 10/2007 | Gaston et al. .................... 606/33 |
| 2008/0125770 | A1 | * | 5/2008 | Kleyman ......................... 606/41 |

OTHER PUBLICATIONS

Elastomeric EMI Shielding Solutions, Laird Technologies, pp. 1-11, 21, from www.lairdtech.thomasnet.com/category/thermal?.
PCT /ISA/237 Written Opinion of the Int'l Searching Authority in PCT US2007/024399 (5 pp).

* cited by examiner

*Primary Examiner* — Nicholas Lucchesi
*Assistant Examiner* — Rebecca E Eisenberg

(57) ABSTRACT

Disclosed is a method and an apparatus for ablating biological tissues, in which a cannula is configured to affect biological tissue and a heat transmitting end-effecter is coupled to the cannula. A source of electromagnetic energy is provided via an electro-magnetic energy emitter and a wall of the heat transmitting end-effecter is made of an electromagnetic-energy-absorbing material that absorbs electromagnetic waves.

13 Claims, 3 Drawing Sheets

THERMAL TREATMENT APPARATUS

PRIORITY

This application claims priority to U.S. patent application Ser. Nos. 61/020,194, filed with the U.S. Patent and Trademark Office Jan. 10, 2008, and 61/143,623, filed with the U.S. Patent and Trademark Office Jan. 9, 2009, the disclosure of each of which is incorporated herein by reference.

BACKGROUND OF INVENTION

1. Field of the Invention

The invention relates to an electromagnetic energy based apparatus for thermal treatment of biological tissues.

2. Description of the Related Art

Conventional devices utilize electromagnetic energy to thermally treat biological tissue. For example, see, e.g. U.S. Pat. Nos. 6,325,796, 6,836,688, 5,697,925, 5,800,493, 5,653,692, 6,443,947, 4,869,248, 5,571,088, 5,474,530 and 5,575,772, the contents of which are incorporated herein by reference. Conventional devices apply electromagnetic energy in microwave or radio frequency range directly to the treated tissue. However, such devices do not allow for fully limiting of the depth of energy penetration into a tissue. As a result, a layer of healthy tissue located behind the treated tissue may be negatively affected. Moreover, these devices do not allow direct control of the temperature in the treated area, and, as a result, the temperature may be higher than required by the procedure and, thus damaging the tissue, or lower than required by the procedure and, thus making the procedure ineffective.

It is, therefore, desirable to provide an apparatus for thermally treating a biological tissue that allows for a relatively brief treatment in a safe and target-oriented manner.

SUMMARY OF THE INVENTION

An aspect of the present invention addresses at least the problems and/or disadvantages and provides at least the advantages described below. Accordingly, an aspect of the present invention is to provide a method and apparatus powered by an electromagnetic energy source to transmit energy, which is then transformed into heat energy that thermally treats a biological tissue, to minimize a period of time necessary to reach a desired temperature.

The present invention also provides an apparatus for thermally treating a biological tissue that has a heat transmitting end-effecter configured with selective electromagnetically-energy-absorbing areas to target diseased tissues while minimizing heat exposure of healthy tissues.

BRIEF DESCRIPTION OF THE DRAWINGS

The above and other features and advantages of exemplary embodiments of the present invention will be more apparent from the following detailed description taken in conjunction with the accompanying drawings, in which.

DETAILED DESCRIPTION OF THE PREFERRED EMBODIMENTS

Figure 1:
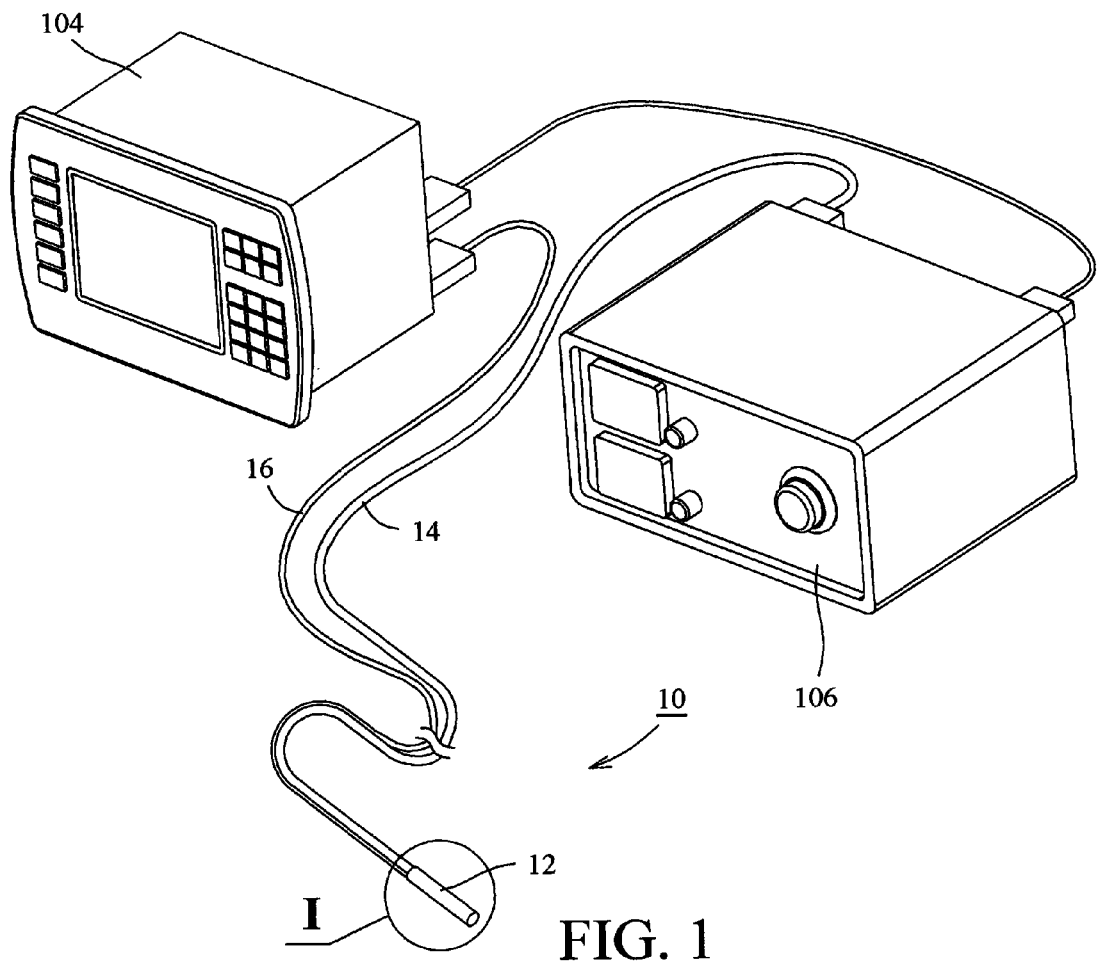
FIG. 1 is a view of a thermal treatment apparatus in accordance with a preferred embodiment of the invention.
Figure 2:
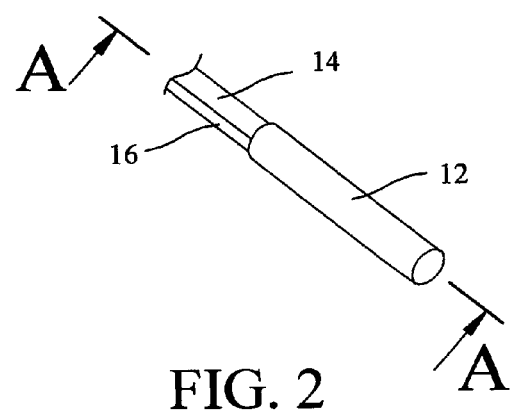
FIG. 2 is a close-up view of an end-effecter of the thermal treatment apparatus of FIG. 1.

Reference will now be made in detail to several views of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity, directional terms, such as rear and front may be used with respect to the drawings. These and similar directional terms should not be construed to limit the scope of the invention in any manner. The term "microwave frequency range" refers herein to frequencies between 30 MHz and 30,000 MHz inclusive, where MHz is one million Hertz, and the term "radio-frequency range" refers herein to frequencies between 30 kHz and 30 MHz, where kHz is one thousand Hertz. Although the following description operates via a microwave energy emitter, the present invention is operable by various electromagnetic energy sources and is not limited to microwave energy.

FIG. 1 provides an overall view of an electromagnetic apparatus for ablation configured in accordance with a preferred embodiment of the invention and operative to perform a thermal treatment of biological tissues. As shown in FIG. 1, cannula 10 includes a heat transmitting end-effecter 12. An electromagnetic generator 106 is coupled to an antenna 24 located within heat transmitting end-effecter 12 via conductive elements or wires 14. In a preferred embodiment, generator 106 is an oscillator that provides a sinusoidal voltage signal. Oscillator 106 is preferably a microwave or radio frequency oscillator.

Figure 3:
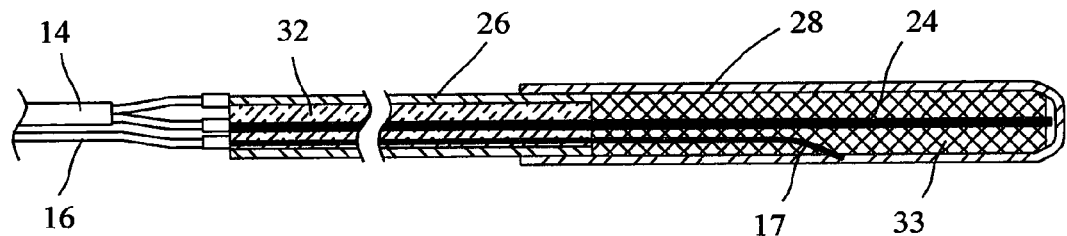
FIG. 3 through FIG. 7 are cross-sectional views along line A-A on FIG. 2 of different embodiments of the end-effecter.

As shown in FIGS. 1 and 3, the temperature of the end-effecter 12 is monitored by a control unit 104 through cable 16 connected to a temperature sensor 17. When excited, antenna 24 emits energy waves that are selectively absorbed by the wall of heat transmitting end-effecter 12, causing the wave absorbing wall regions to heat. In a preferred embodiment in which the energy is transmitted through a layer of air, as shown on FIG. 4 though FIG. 6, oscillator 106 provides for rapid heating of the wave absorbing regions of heat transmitting end-effecter 12, effectively heating diseased tissue in a time-effective, safe operation.

Referring to FIG. 2 through FIG. 7, the wires 14 are coupled to a wall element 26 and antenna 24. Wall element 26 is constructed as an outer coaxial cable conductor, preferably coated or covered by electrical and heat insulators such as nylon, polypropylene or Teflon®. The antenna 24 and wall element 26 are electrically isolated relative to one another by an insulator 32. In certain preferred embodiments, wall element 26, insulator 32, and antenna 24 may be a coaxial cable having an inner conductor thereof extended beyond the wall element 26 and insulator 32.

The antenna 24 is located within a heat transmitting outer shell 28. The antenna 24 propagates energy waves within heat transmitting end-effecter 12. For certain medical procedures, such as where the end-effecter is inserted into a blood vessel and forced to follow the path of the blood vessel to a treatment area, outer shell 28 is preferably constructed of substantially flexible material. In alternative embodiments utilized for medical procedures in which the end-effecter is directly inserted in the treated tissue, outer shell 28 is constructed from a substantially rigid material.

In a preferred embodiment, the material of the outer shell 28 is substantially flexible, silicone impregnated with silver (Ag) and glass fillers, which are generally unaffected by exposure to temperatures reaching 500° F. Glass fillers can be regular glass in form of small beads and other fillers include nickel (Ni), copper (Cu), Aluminum (Al), which can each be used as a single filler or combined with other materials, for example combinations of Ag/Cu; Ag/Al; Ag/Ni; Ag/Glass. Silicone is a preferred material due to compatibility to the human body, and other materials that can be used include fluorosilicone, fluorocarbon, thermoplastic rubber and ethyline propylene diene monomer. When used for a substantially rigid outer shell, thermoplastic materials, such as rigid urethane impregnated with polyamide and thermoplastic urethane impregnated with carbonyl iron powder, iron silicide and ferrites fillers are utilized, in view of advantageous microwave absorbing properties.

In a preferred embodiment, heated regions on the wall of the outer shell 28 are provided by filling the regions with electromagnetic energy absorption particles, wherein the particles include nickel, nickel-plated graphite, silver-plated aluminum, silver-plated copper, silver-plated nickel, silver-plated glass and pure silver.

Figure 4:
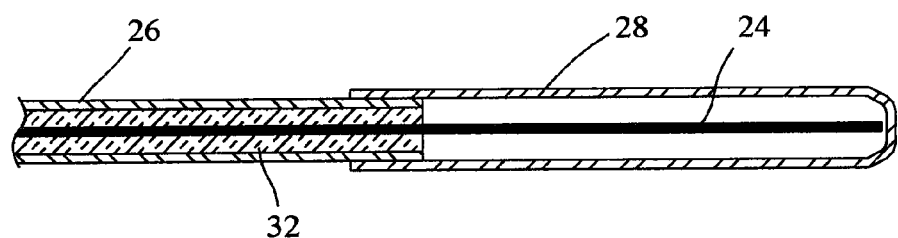
Figure 5:
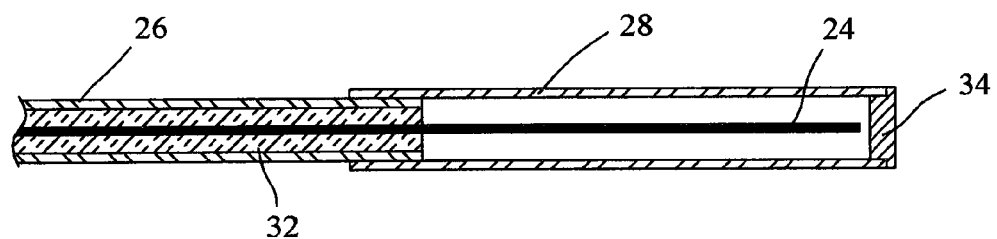
Figure 6:
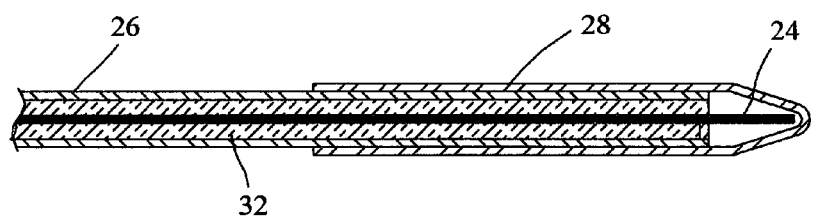
Figure 7:
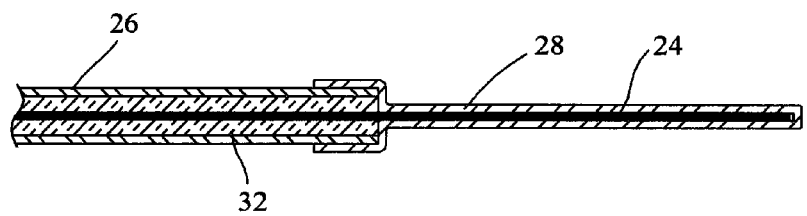

In the embodiments shown in FIG. 3 through FIG. 7 the particles are distributed over the entire wall of the outer shell 28. Thus, electromagnetic waves emitted by antenna 24 propagating through the layer of air, as shown in FIG. 4 through FIG. 6, or the layer of isolating material as shown by the embodiment presented on FIG. 3, or directly to the walls of the outer shell 28, as shown by the embodiment presented on FIG. 7. When impinging upon the particles, electromagnetic energy is transferred into heat energy manifested at the particles. In FIG. 5, a biologically inert insulator 34 forms a cap on the end of heat-transmitting end-effecter 12.

In another preferred embodiment, the wave-absorption particles may be coated on a surface of outer shell 28, which is made out a regular elastomer such as silicone. The wave-absorption particles in one embodiment cover the entire surface of outer shell 28 and in other embodiments are coated in a pattern. Preferable coating patterns include longitudinal stripes, latitudinal stripes, mesh and series of dots, with the distance between the stripes or dots preferably arranged to place the dots at a distance smaller that a length of the wave emitted by the antenna, to preclude wave energy escaping from the endeffecter. Dots are a preferred embodiment for maintaining flexibility, with an aperture between dots being sized smaller than the emitted wavelength.

As shown, the outer shell 28 can be formed into various shapes and dimensioned to address specific needs of any given anatomical site or patient. Selective shaping provides a further benefit of reducing the impact of reflection.

Figure 8:
FIG. 8 is a schematic view of power supply and control systems.

Referring to FIGS. 1 and 8, the operation of the apparatus is described in treating a patient. The electromagnetic generator 106 excites antenna 24 through wires 14. The antenna 24 produces waves in a pre-selected range of frequencies that are absorbed by the electromagnetic energy absorption particles of the elastomeric material in the heat transmitting outer shell 28. The electromagnetic energy absorbed by the electromagnetic energy absorption particles is transformed into heat energy, which thermally treats the tissue by exposure to elevated temperature.

The temperature elevation sufficient to cause the required thermal effect is provided via electromagnetic energy from the electromagnetic generator, preferably absorbed by the electromagnetic energy-absorption particles of the conductive elastomeric material. Generally, the level of the generated electromagnetic energy is selected to reach the maximum ablation temperature in a shortest period of time, in order to reduce treatment time and minimize undesirable heat transfer to neighboring healthy tissue. See, e.g., patent application Ser. No. 11/603,866 filed Nov. 24, 2006, and U.S. Pat. Nos. 5,843,144, 5,902,251, 6,041,260, 6,366,818 and 6,447,505, the contents of each of which is incorporated by reference herein. As shown in FIG. 3, temperature sensor 17 is coupled to controller 104 and is utilized to monitor the temperature of the heat transmitting end-effecter periphery. Controller 104 controls power source 106 to maintain the desired temperature.

While the invention has been shown and described with reference to exemplary embodiments thereof, it will be understood by those skilled in the art that various changes in form and details may be made therein without departing from the spirit and scope of the invention, as defined by the following claims.

What is claimed:

1. An apparatus for ablating biological tissues, the apparatus comprising:
   a heat transmitting end-effecter; and
   a microwave energy emitter connected to receive microwave energy from a source of microwave energy,
      wherein the heat transmitting end-effecter includes a heat transmitting outer shell made of an microwave energy absorbing material and the microwave energy emitter is positioned inside of the heat transmitting end-effecter,
      wherein the heat transmitting outer shell of the heat transmitting end-effecter absorbs energy supplied by the microwave energy emitter and provide a corresponding heat energy therefrom, and
      wherein the heat transmitting end-effecter directly contacts the biological tissue to absorb said heat energy from said outer shell, transferring heat from said outer shell directly to the biological tissue.

2. The apparatus of claim 1, wherein the heat transmitting outer shell made of microwave energy absorbing material including microwave-absorbing particles.

3. The apparatus of claim 2, wherein the microwave-absorbing particles include nickel, nickel-plated graphite, silver-plated aluminum, silver-plated copper, silver-plated nickel, silver-plated glass, pure silver, fluorosilicone, fluorocarbon, and ethylene-propylene terpolymer (EPDM).

4. The apparatus of claim 2 wherein said wave-absorbing particles are disposed in shapes and patterns at relative distances smaller than the wavelength of the energy emitted by said microwave energy emitter.

5. The apparatus of claim 2, wherein said microwave energy emitter comprises an elongated antenna having an end connected to one cable conductor, said one cable conductor also being connected to a source of microwave energy.

6. The apparatus of claim 1, wherein the outer shell is constructed of silicon impregnated with at least one of glass fillers, silver, nickel, copper and aluminum.

7. The apparatus of claim 1, wherein the outer shell is constructed of substantially flexible material.

8. The apparatus of claim 1, wherein the outer shell is constructed of substantially rigid material.

9. The apparatus of claim 1, wherein the microwave energy emitter directly contacts the heat transmitting outer shell of the heat transmitting end-effecter.

10. The apparatus of claim 1, wherein the microwave energy emitter is spaced from the heat transmitting outer shell of the heat transmitting end-effecter.

11. The apparatus of claim 1 wherein the outer shell is constructed of thermoplastic impregnated with at least one of polyamide, carbonyl iron powder, iron silicide and ferrite powders.

12. The apparatus of claim 1, further including a temperature sensor disposed to monitor said end-effecter periphery temperature.

13. The apparatus of claim 1, wherein said microwave energy emitter is connected to a controllable source of microwave energy, said apparatus further comprising a controller connected to monitor said temperature sensor and to said controllable source of microwave energy to provide control thereof in response to temperature sensor to maintain a desired end-effecter periphery temperature.

\* \* \* \* \*